United States Patent
Doyle et al.

(10) Patent No.: US 9,265,903 B2
(45) Date of Patent: Feb. 23, 2016

(54) VENTILATION VITALITY RING

(71) Applicant: Covidien LP, Mansfield, MA (US)

(72) Inventors: Peter Doyle, Vista, CA (US); Kadri Jabri, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/287,729

(22) Filed: May 27, 2014

(65) Prior Publication Data

US 2015/0343160 A1     Dec. 3, 2015

(51) Int. Cl.
    *G08B 5/00*     (2006.01)
    *A61M 16/00*     (2006.01)
    *A61M 16/06*     (2006.01)

(52) U.S. Cl.
    CPC ....... *A61M 16/0003* (2014.02); *A61M 16/0051* (2013.01); *A61M 16/0057* (2013.01); *A61M 16/06* (2013.01); *A61M 2205/18* (2013.01); *A61M 2205/3368* (2013.01); *A61M 2205/52* (2013.01); *A61M 2205/583* (2013.01); *A61M 2230/202* (2013.01); *A61M 2230/205* (2013.01)

(58) Field of Classification Search
    CPC ..................... A61M 2205/583; G06F 19/3487
    USPC ............ 340/815.4, 691.1, 691.6; 128/205.23, 128/204.23; 600/440
    See application file for complete search history.

(56) References Cited

U.S. PATENT DOCUMENTS

| | | | | |
|---|---|---|---|---|
| 5,881,723 | A * | 3/1999 | Wallace et al. | 128/204.21 |
| 5,931,160 | A * | 8/1999 | Gilmore et al. | 128/204.21 |
| 6,369,838 | B1 * | 4/2002 | Wallace et al. | 715/810 |
| 8,217,946 | B2 | 7/2012 | Halpern et al. | |
| 8,595,639 | B2 * | 11/2013 | Milne et al. | 715/771 |
| 8,638,200 | B2 * | 1/2014 | Milne et al. | 340/286.07 |
| 9,072,848 | B2 * | 7/2015 | Bertinetti et al. | 1/1 |
| 2004/0186357 | A1 | 9/2004 | Soderberg et al. | |
| 2005/0209515 | A1 | 9/2005 | Hockersmith et al. | |
| 2008/0021287 | A1 | 1/2008 | Woellenstein et al. | |
| 2011/0201911 | A1 | 8/2011 | Johnson et al. | |

FOREIGN PATENT DOCUMENTS

WO     2009/132434 A1     11/2009

\* cited by examiner

*Primary Examiner* — Toan N Pham
(74) *Attorney, Agent, or Firm* — Carter, DeLuca, Farrell & Schmidt, LLP (57) ABSTRACT

A system and method for displaying the status of a patient on ventilation is disclosed including a ventilator system configured to provide mechanical ventilation to a patient and a display device operatively associated with the ventilator system. The display device is configured to display a user interface including a pictogram having patient status information related to the ventilator system. The pictogram includes a central section configured to display patient status information relating to an overall status of the patient and at least one group section configured to display patient status information relating to a particular category of ventilatory status parameters.

20 Claims, 3 Drawing Sheets

VENTILATION VITALITY RING

TECHNICAL FIELD

The present disclosure relates generally to patient monitoring and to systems and methods for monitoring patients on mechanical ventilation.

BACKGROUND

Mechanical ventilation is often an essential, life-saving therapy for critically ill patients and patients experiencing respiratory failure. Critical care ventilators provide ventilator support and display patient data to assist caregivers with determining the ventilatory status of a patient. Current generation critical care ventilators provide caregivers with a large quantity of information from which to make critical determinations about the patient's status. For example, ventilatory data is typically provided in the form of graphs, numbers, and other similar elements shown on one or more status screens.

SUMMARY

The present disclosure relates to systems and methods for displaying a status of a patient on ventilation. Systems provided in accordance with the present disclosure include, for example, a ventilator system and a display device. The display device is configured to display a user interface including a pictogram having patient status information related to the ventilator system. The pictogram includes a central section configured to display patient status information relating to an overall status of the patient and at least one group section configured to display patient status information relating to a particular category of ventilatory status parameters.

The present disclosure is advantageous in that it provides a clinician with patient status information in an easy to understand format for a quick review of the patient's ventilatory status. For example, the present disclosure provides the clinician with a colored pictogram containing condensed high level status information that allows the clinician to make a quick assessment and determination of the patient's status at a glance without having to personally assess or compare actual patient ventilatory status parameters with associated threshold values relating to the patient's condition. By providing a color coded pictogram, the clinician may also easily assess the patient's status from a distance without having to approach a ventilator and read specific text such as numbers or letters.

Certain embodiments of the present disclosure may include some, all, or none of the above advantages and/or one or more other advantages readily apparent to those skilled in the art from the drawings, descriptions, and claims included herein. Moreover, while specific advantages have been enumerated above, the various embodiments of the present disclosure may include all, some, or none of the enumerated advantages and/or other advantages not specifically enumerated above.

BRIEF DESCRIPTION OF THE DRAWINGS

The present disclosure and its various aspects and features are described hereinbelow with reference to the accompanying drawings, wherein.

DETAILED DESCRIPTION

Provided in accordance with the present disclosure are systems and methods for monitoring a patient on a mechanical ventilator and displaying the patient's status for review by a clinician. The display may include a pictogram which provides visual indicators of ventilator-related categories such as, for example, ventilation, oxygenation, gas exchange, lung protection, and weaning. Each category includes a visual indicator that indicates the quality of patient performance in that category and can be used to simplify the clinician's initial review of the patient status by providing a concise assessment of the patient's status in each category. In addition, the pictogram provides a central section including a visual indicator and numerical value that indicates the overall quality of the patient's performance and provides a concise assessment of the patient's overall status.

As used herein, the term "clinician" includes doctors, nurses, caregivers, or any other medical personnel associated with the patient or that is in charge of reviewing or monitoring the patient's health status. In addition, the term "clinician" may also include hospital staff that determine and set criteria and parameters for use with ventilators.

Although the systems and methods provided herein are described with reference to medical ventilation, the systems and methods provided herein may also be utilized in other medical fields requiring patient monitoring including, for example, cardiac monitoring, where each category relates to a cardiac related variable, for example, hemodynamics and other cardiac related variables. Use in other medical fields requiring patient monitoring are also contemplated where, for example, the clinician may set the pictogram and categories as needed to correspond to the particular medical field.

Figure 1:
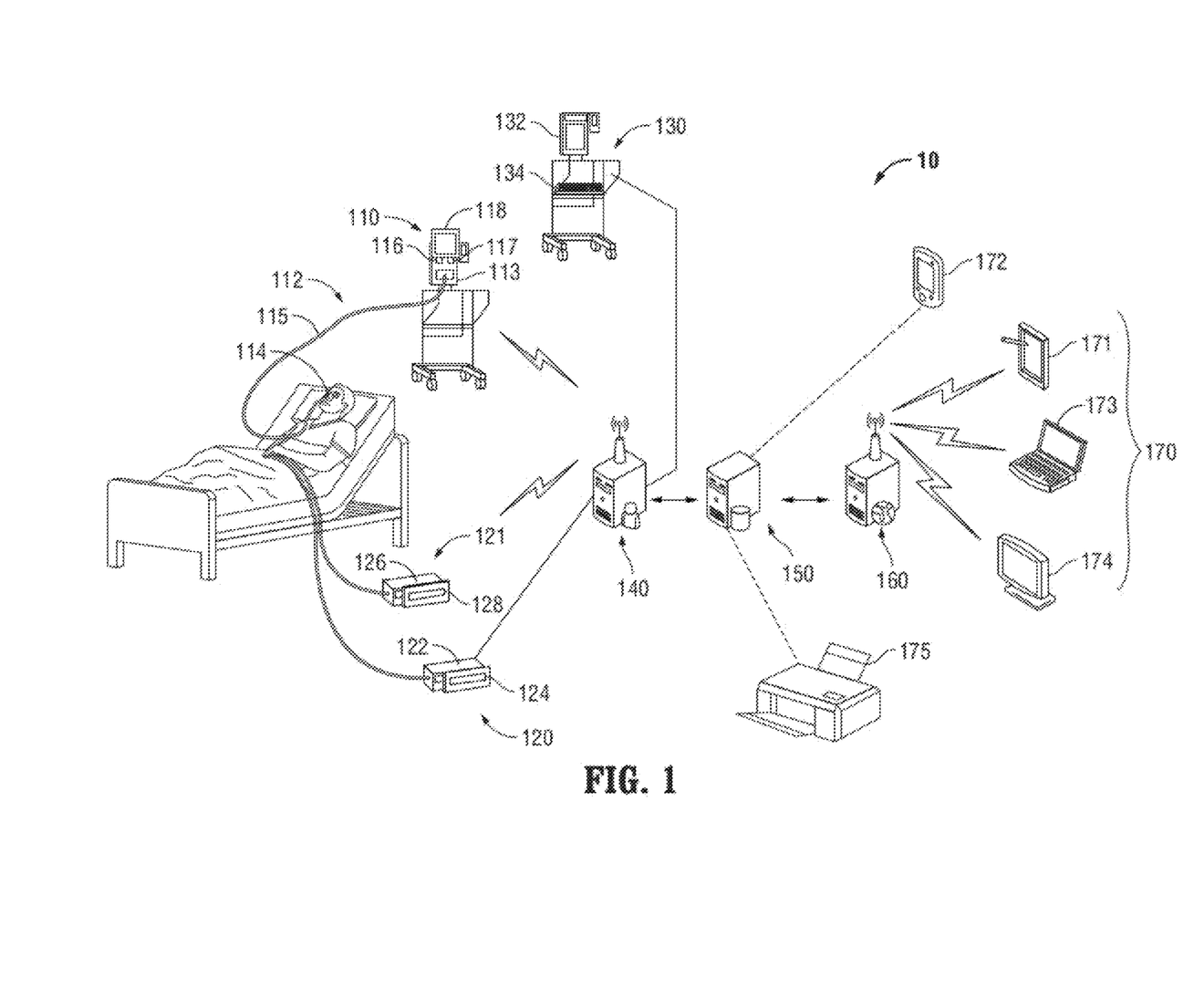
FIG. 1 is a schematic illustration of a patient care and monitoring system provided in accordance with the present disclosure.

Referring to FIG. 1, an exemplary system provided in accordance with the present disclosure is shown generally identified by reference numeral 10. System 10 includes one or more patient care devices 110, one or more patient monitoring devices 120, 121, one or more bedside devices 130, one or more data servers 140, one or more application servers 150, one or more web servers 160, and one or more remote devices 170. For the purposes herein, exemplary system 10 is generally described, although the aspects and features of the present disclosure may be implemented, incorporated, or utilized with any other devices, systems, and combinations thereof.

The one or more patient care devices 110 may include, for example, a ventilator system 112. Ventilator system 112 may be any suitable ventilator system, e.g., the Puritan Bennett™ 840 Ventilator System sold by Covidien LP of Boulder, Colo., USA, and generally includes a bedside ventilator unit ("ventilator") 113, a patient interface member 114, e.g., an artificial airway (for invasive ventilation) or mask (for noninvasive ventilation), and a ventilator circuit 115, e.g., an inspiratory and expiratory limb, interconnecting the ventilator 113 and patient interface member 114. The ventilator 113 controls the supply of oxygenated air to the patient and includes at least a first input 116 for allowing a user to set a desired $FiO_2$ level and a second input 117 for allowing a user to set a desired PEEP. Ventilator 113 may further include a display 118 for displaying relevant data relating to ventilator system 112 and/or the patient. Ventilator 113 may be coupled to one or more servers 140, 150, 160, e.g., data server 140, either wirelessly or via a wired connection. Ventilator 113 may include any suitable software, firmware, and hardware for the above purposes.

Patient interface member 114 may include, for example, a capnography monitor that may be configured for obtaining $CO_2$ readings from the patient during exhalation. The capnography monitor included in patient interface member 114 may be configured to display $CO_2$ readings on display 118 of ventilator 113 and/or may also be configured to relay the $CO_2$ readings to one or more servers 140, 150, 160, e.g., data server 140 via a wireless or a wired connection to ventilator 113.

The one or more patient monitoring devices 120, 121 may include any suitable device(s) for visual monitoring, audible monitoring, monitoring of physical characteristics, physiological conditions, other measurable characteristics or conditions, etc. For example, patient monitoring devices 120, 121 may be a temperature sensor 122 and a pulse oximeter 126, respectively. Temperature sensor 122 may be configured to display temperature data on a visual display 124 thereof, on display 118 of ventilator 113, and/or to relay temperature data to one or more servers 140, 150, 160, e.g., data server 140. Temperature sensor 122 may be wirelessly coupled to data server 140, or may be coupled to data server 140 via a wired connection.

Pulse oximeter 126 may be configured to measure the $SpO_2$ at a particular location (or locations) on the patient and to relay the same to portable monitoring device 121. Pulse oximeter 126 may be configured for obtaining a $SpO_2$ reading at specific intervals. The intervals at which readings are taken may be constant, e.g., one reading every second, or may be taken manually upon request. Portable monitoring device 121 may be configured to process and display the $SpO_2$ data on a visual display 128 thereof, on display 118 of ventilator 113, and/or may be configured to relay the $SpO_2$ data to one or more servers 140, 150, 160, e.g., data server 140. This may be done wirelessly as shown with respect to portable monitoring device 121, or as a wired connection as shown with respect to portable monitoring device 120. Additional monitoring devices may similarly be employed to monitor other characteristics, conditions, or to otherwise monitor the patient and to process the patient data, display the patient data, and/or relay the patient data to data server 140. The patient monitoring devices may be wirelessly coupled to data server 140, or may be coupled to data server 140 via a wired connection. The patient monitoring devices may include any suitable software, firmware, and/or hardware for the above-noted purposes.

Bedside device 130 may include a display 132 and a user input 134, e.g., a touch-screen display or keyboard and mouse. Bedside device 130 is employed to display relevant parameters, conditions, sensed data, and/or other patient information on display 132 at a patient's bedside. Bedside device 130 is further configured to receive user input data via user input 134 for display on display 132 and/or for transmission to data server 140 (and/or the other servers 150, 160). Exemplary information input into bedside device 130 may include medical care information (e.g., the patient's drug administration schedule), control parameters, other measured data, and/or biographical or other observed data/notes. Bedside device 130 may be wirelessly coupled to data server 140, or may be coupled to data server 140 via a wired connection. Bedside device 130 may include any suitable software, firmware, and hardware for the above purposes. Alternatively or additionally to bedside devices 130, patient monitoring devices 120, 121, and patient care devices 110, information relating to the patient may be automatically pulled from another system, e.g., a patient's Electronic Medical Record (EMR), an Admission, Discharge, and Transfer (ADT) electronic file, lab data, etc. This information may be utilized directly and/or may be used in determining any of the other information, e.g., control parameters or other settings, as will be detailed below.

Data server 140, application server 150, and web server 160 are coupled to one another and between remote devices 170 and the local devices, e.g., ventilator system 112, temperature sensor 122, pulse oximeter 126, and bedside device 130, for storing, processing, and/or transmitting information therebetween. More specifically, one or more of servers 140, 150, 160, e.g., data server 140, are configured to store information, e.g., the parameters, conditions, sensed data, reports, and/or other information, in a database and to process the information. Servers 140, 150, 160 are further configured to cooperate with one another to transmit information between the servers 140, 150, 160, other systems (e.g., a patient's EMR, an ADT electronic file, lab data, etc.), ventilator system 112, temperature sensor 122, pulse oximeter 126, bedside device 130, and/or remote devices 170. Servers 140, 150, 160 may include any suitable software, firmware, and hardware for these purposes and may establish the above-described communication via wired and/or wireless communication.

Remote devices 170 request and receive information, e.g., the parameters, conditions, sensed data, and/or other information, process the information, if needed, and display the information to a user, e.g., via a display monitor, user interface, browser, and/or application running on the remote device 170, or otherwise output the information to a user, e.g., print a generated report containing the information. Remote devices 170 may further be configured to receive input from a user, e.g., to input information, control the display or output of the information, set parameters, reset notifications, etc. Information input into remote devices 170 may include medical care information (e.g., the patient's drug administration schedule), control parameters, other measured data (e.g., the patient's WBC), and/or biographical or observed data. Remote devices 170 may include one or more tablet PCs 171, smartphones 172, laptop computers 173, display monitors 174, printers 175, or other suitable devices and may incorporate any suitable software, firmware, and hardware for the above purposes.

Figure 2:
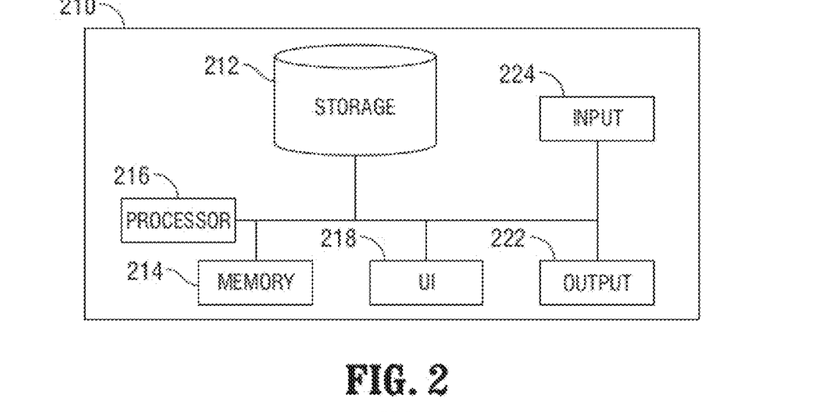
FIG. 2 is a schematic illustration of a hardware and software configuration for use with the system of FIG. 1.

Turning now to FIG. 2, in conjunction with FIG. 1, one configuration of hardware and software components for receiving/transmitting information, e.g., control parameters, conditions, sensed data, and/or other information, processing the information, receiving user input, and/or displaying the information or otherwise outputting the information in accordance with the present disclosure is shown generally identified by reference numeral 200. Configuration 200 may be embodied within one or more of patient care devices 110, patient monitoring devices 120, 121, bedside devices 130, servers 140, 150, 160, and remote devices 170, or may be implemented across one or more of patient care devices 110, patient monitoring devices 120, 121, bedside devices 130, servers 140, 150, 160, and remote devices 170. That is, receiving/transmitting the information and user input, processing the information, and outputting the information for control, display, or other output may be performed locally, e.g., at one of patient care devices 110, patient monitoring devices 120, 121, bedside devices 130; on one or more servers 140, 150, 160 for distribution to the various devices 110, 120, 121, 130, 170, e.g., across a network; at the remote devices 170 themselves; or in any combination of the above. For the purposes of simplicity, configuration 200 will be described herein as embodied in a system 210, keeping in mind that system 210 may be incorporated into or across any or all of the components of system 10.

System 210 generally includes a storage 212, a memory 214, a processor 216, a user interface (UI) 218, an output 222, and an input 224. Storage device 212 may include any suitable component(s) operable for storing information received via input 224, such as, for example, a magnetic disk, flash memory, optical disk, or other suitable data storage device. Memory 214 may include any computer memory, e.g., RAM or ROM, mass storage media, removable storage media, combinations thereof, or any other suitable computer-readable storage medium, storing instructions for causing processor 216 to execute particular functions, e.g., to process the information. Processor 216 may include any suitable component(s), e.g., a central processing unit (CPU), operable to execute instructions stored in memory 214 to process and manipulate information, e.g., stored in storage device 212 or received via input 224, for output to UI 218 or output 222. UI 218 is displayed on any of the display devices mentioned above including, for example, display 118 of ventilator 113, display 132 of bedside devices 130, or the displays of remove devices 170. Processor 216 is further configured to receive, via input 224 and/or UI 218, information, data, and/or control parameters for processing and manipulating the information in accordance with user-selected settings and user input. UI 218 functions to output the processed information for visual display, e.g., in graphical and/or numerical form, to the user and/or allows for the input of information, data, setting of parameters, etc., by the user. Output and input 222, 224, respectively, are provided to facilitate communication between system 210 and the other components of system 10. In particular, input 224 is configured to receive information to be processed, e.g., data from ventilator system 112, temperature sensor 122, pulse oximeter 126, and bedside device 130 (or other device where user-input data is provided).

Figure 3:
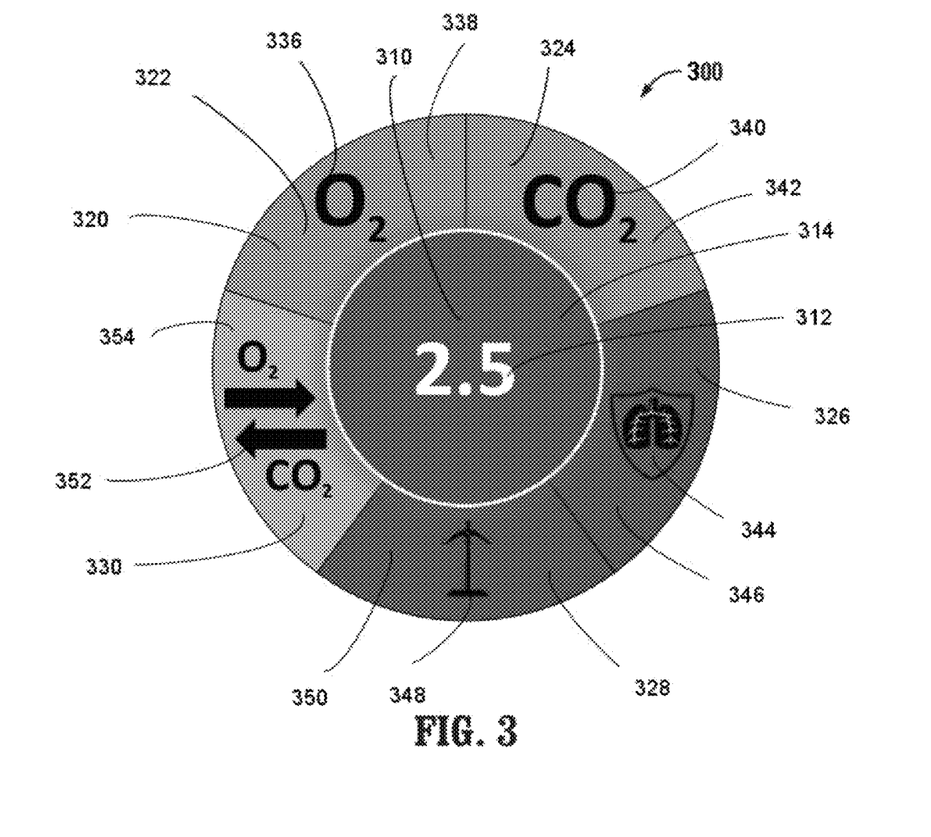
FIG. 3 illustrates a pictogram provided in accordance with the present disclosure, as presented to a user.

With reference to FIG. 3, a pictogram 300 in accordance with embodiments of the present disclosure is shown displaying exemplary information as output by UI 218 to any of the displays described above. Pictogram 300 may be the only component initially displayed by UI 218 or may be one of many components displayed by UI 218 at the same time. Pictogram 300 provides a user, for example, a clinician or other medical personnel, with concise information about the patient's status in an easy to understand format.

As used herein, the term "patient status information" includes any patient status information received from devices associated with the patient, for example, medical devices, ventilators, sensors, or other similar devices, medical records, medical background, disease history, and any other item of patient status information that may be relevant to the treatment of the patient.

For example, pictogram 300 includes a central section 310 and number of specific group sections 320 surrounding the central section 310. In the example shown in FIG. 3, central section 310 is displayed as a circular shape with group sections 320 forming a ring fully surrounding or at least partially surrounding central section 310. Pictogram 300, central section 310, and/or group sections 320 may alternatively be formed in other shapes, for example, squares, rectangles, triangles, ellipsoids, other polygons, or other similar shapes, without departing from the scope of the present disclosure. Central section 310 may alternatively fully surround or at least partially surround group sections 320 without departing from the scope of the present disclosure.

Central section 310 provides a clinician with a concise understanding of the overall status of the patient's condition. As an example, central section 310 may display patient status information including the patient's overall status as a number, a color, other similar visual indicators or other forms of communicating the patient's status. In the pictogram 300 shown in FIG. 3, for example, the patient status information is displayed in central section 310 as a number component 312 and a background component 314. The patient status information may alternatively be displayed as only the number component 312, only the background component 314, or in any combination of the number component 312, background component 314, and any other additional components without departing from the scope of the present disclosure.

The number component 312 may be based on a number scale, for example, from 0.0 to 10.0. As an example, a patient in good condition may have a number component 312 that is near or at 10.0 while a patient in bad condition that requires attention may have a number component 312 that is near or at 0.0. Alternative number scales may also be utilized depending on clinician and/or hospital preference and the particular number scale to be displayed by number component 312 may be adjustable by the clinician. Number component 312 may be based on a combination of various patient parameters, conditions, sensed data, and/or other information. For example, the parameters, conditions, values, sensed data, and/or other outputs of each group section 320 described below may contribute to the displayed number component 312. The parameters, conditions, values, sensed data, and/or other outputs from each of group sections 320 may also have different weights in determining the value of number component 312. The weighting for each group section 320 may also automatically increase as the duration that the parameters, conditions, values, sensed data, and/or other outputs from one of the group section 320 is above or below a certain threshold increases.

In addition to number component 312, background component 314 of central section 310 provides the clinician with an instantly recognizable indicator of the patient's condition. For example, a visual indicator displayed by background component 314 may be correlated with the number component 312 and may display a different visual indicator based on the patient's current status, e.g., the patient's current value of the number component 312. As an example, the visual indicator may be displayed as a shape, a color, and/or any other suitable indicator for displaying the patient's status. For example, the color of background component 314 may vary between green, yellow, orange, and red depending on the patient's condition and current status where green may indicate a good patient status, yellow may indicate a moderately good patient status, orange may indicate a fair patient status, and red may indicate a poor patient status. For example, background component 314 may be displayed as green when the value of number component 312 is greater than a first threshold, for example, 7.5, may be displayed as yellow when the value of number component 312 is greater than a second threshold, for example, 5.0, and less than or equal to the first threshold, may be displayed as orange when the value of number component 312 is greater than a third threshold, for example, 2.5, and less than or equal to the second threshold, and may be displayed as red when the value of the number component 312 is less than or equal to the third threshold. Likewise a shape of the background component 314 may also change depending on the patient's status. For example, the shape of background component 314 may change from a circle to a square, triangle, or any other shape based on the value of number component 312 relative to a threshold as described above for the color. The number of thresholds and the threshold values for displaying different colors, shapes, and/or other visual indicators in background component 314, and the colors, shapes, and/or other visual indicators to be displayed for each threshold may be adjusted by the clinician. Additional threshold values may also be added and additional colors, shapes, and/or other visual indicators may be displayed by background component 314 based on the additional threshold values without departing from the scope of the present disclosure.

Each group section 320 provides patient status information to the clinician with respect to a specific subset or category of patient parameters. In the pictogram 300 shown in FIG. 3, for example, a group section 322 provides patient status information relating to the patient's oxygenation levels, a group section 324 provides patient status information relating to the patient's ventilation levels, a group section 326 provides patient status information relating to the patient's lung protection levels, a group section 328 provides patient status information relating to the patient/ventilator work levels and weaning, and a group section 330 provides patient status information relating to the patient's gas exchange levels. The clinician may add or remove group sections 320 from pictogram 300 relating to specific patient parameters or categories as necessary for specific patient and/or clinician requirements. For example, group section 320 may include one group section, two group sections, five group sections as shown in the example of FIG. 3, or any number of group sections, as necessary to meet clinician and clinical requirements.

Each group section 320 includes a symbol and a background. The Symbol provides the clinician with an indication or identification of the particular group section 320 that is displayed in pictogram 300 while the background provides the clinician with an indication of the status of the particular group section 320. Each background may provide a visual indicator, for example, a color-coded status indicator, a shape based status indicator, or other similar status indicators, to the clinician based on the status of the particular group section 320 being observed.

As further illustrated in FIG. 3, group section 322 displays a symbol 336 as "$O_2$" which identifies to the clinician that group section 322 is related to oxygenation. As an example, the color of a background 338 displayed by group section 322 may be based on a comparison of the $SpO_2$ readings from pulse oximeter 126 with pre-determined or adjustable thresholds. The thresholds may be adjusted by the clinician as necessary for a particular patient or patient condition. Examples of some thresholds include an $SpO_2$ reading greater than a threshold value of 95% which may indicate normal oxygenation in the patient and may be displayed by background 338 as the color green, an $SpO_2$ reading from 90% and 95% which may indicate that the patient is experiencing mild hypoxemia and may be displayed by background 338 as the color yellow, an $SpO_2$ reading from 76% and 89% which may indicate that the patient is experiencing moderate hypoxemia and may be displayed by background 338 as the color orange, and an $SpO_2$ reading of less than or equal to 75% which may indicate that the patient is experiencing severe hypoxemia and may be displayed by background 338 as the color red. The number of thresholds and the threshold values for displaying different colors in background 338, and the colors to be displayed for each threshold may be adjusted by the clinician. As mentioned above, the color of background component 314 and number component 312 of central section 310 may be based at least in part on the threshold comparisons described above for group section 322 where the comparisons in group section 322 may receive a different weighting than the other group sections 320. For example, group section 322 which correlates to oxygenation may represent 40% of the overall score value for the numerical component 312 while the remaining sections may represent 60% of the overall score value for numerical component 312. For example, when there are five group sections 320, the remaining group sections 320 may each represent 15% if the remaining group sections 320 are equally weighted. Other weighting percentages for each group section 320 are also contemplated and the weighting for each group section 320 may be adjusted by the clinician. With continued reference to FIG. 3, group section 324 displays a symbol 340 as "$CO_2$" which identifies to the clinician that group section 324 is related to alveolar ventilation. As an example, the color of a background 342 displayed by group section 324 may be based on a comparison of the end tidal carbon dioxide partial pressure ($etCO_2$) readings from the capnography monitor included in patient interface member 114, or any other device that measures ventilation $etCO_2$ from the patient, with pre-determined or adjustable thresholds. The thresholds may be adjusted by the clinician as necessary for a particular patient or patient condition. Examples of some thresholds include an $etCO_2$ reading from 35 to 45 mmHg which may indicate normal ventilation and may be displayed by background 342 as the color green, an $etCO_2$ reading of less than 35 mmHg which may indicate that the patient is experiencing an increase in dead space ventilation, where areas of the lung are ventilated but not perfused, and may be displayed by background 342 as the color yellow or red depending on the severity of the condition, and an $etCO_2$ reading greater than 45 mmHg which may indicate that the patient is experiencing hypoventilation, e.g., elevated carbon dioxide, and may be displayed by background 342 as the color yellow or red depending on the severity of the condition. As an example, an etCO2 reading of 34 or 46 may be displayed by background 342 as the color yellow while an etCO2 reading of 25 or 55 may be displayed by background 342 as the color red. The number of thresholds and the threshold values for displaying different colors in background 342, and the colors to be displayed for each threshold may be adjusted by the clinician. As mentioned above, the color of background component 314 and number component 312 of central section 310 may be based at least in part on the threshold comparisons described above for group section 324 where the comparisons in group section 324 may receive a different weighting than the other group sections 320.

Still referring to FIG. 3, group section 326 displays a symbol 344 as a lung which identifies to the clinician that group section 326 is related to lung protection. As an example, the color of a background 346 displayed by group section 326 may be based on the comparison of tidal volume (Vt) and plateau pressure (Pplat) readings measured from the patient with pre-determined or adjustable thresholds. The thresholds may be adjusted by the clinician as necessary for a particular patient or patient condition. For example, the thresholds and settings of Vt and Pplat may be adjusted for patients having chronic conditions or pre-injured lungs. Examples of some thresholds for Vt include a Vt reading from 5 to 7 ml/kg which may indicate normal tidal volume and may be displayed by background 346 as the color green, a Vt reading greater than or equal to 7 ml/kg which may indicate that the patient is experiencing a moderately high tidal volume and may be displayed by background 346 as the color yellow, and a Vt reading greater than 10 ml/kg which may indicate that the patient is experiencing a high tidal volume and may be displayed by background 346 as the color red. Examples of some thresholds for Pplat include a Pplat less than 32 cmH$_2$O which indicates a safe plateau pressure and may be displayed by background 346 as the color green, and a Pplat greater than or equal to 32 cmH$_2$O which may indicate a high plateau pressure and may be displayed by background 346 as the color yellow or red. The color of background 346 may also be based on a combination of both Vt and Pplat where, for example, even if each of Vt and Pplat individually would only trigger a threshold for displaying the color yellow by background 346, background 346 may still display the color red since both Vt and Pplat are out of the normal range. The number of thresholds and the threshold values for displaying different colors in background 346, and the colors to be displayed for each threshold may be adjusted by the clinician. As mentioned above, the color of background component 314 and number component 312 of central section 310 may be based at least in part on the threshold comparisons described above for group section 326 where the comparisons in group section 326 may receive a different weighting than the other group sections 320.

With further reference to FIG. 3, group section 328 displays a symbol 348 which identifies to the clinician that group section 328 is related to weaning and patient/ventilator work of breathing (WOB). As an example, the color of a background 350 displayed by group section 328 may be based on a comparison of the patient WOB readings measured by the ventilator with pre-determined or adjustable thresholds. The thresholds may be adjusted by the clinician as necessary for a particular patient or patient condition. Examples of some thresholds include a WOB reading from 0.2 to 0.7 J/L which may indicate a normal patient WOB and may be displayed by background 350 as the color green, a WOB reading of less than 0.2 J/L which may indicate that the patient is experiencing a lower than normal WOB and may be displayed by background 350 as the color yellow or red depending on the severity of the condition, a WOB reading from 0.7 to 1.2 J/L which may indicate that the patient is experiencing a moderate WOB and may be displayed by background 350 as the color yellow and a WOB reading greater than 1.2 J/L which may indicate that the patient is experiencing a high WOB and may be displayed by background 350 as the color red. The number of thresholds and the threshold values for displaying different colors in background 350, and the colors to be displayed for each threshold may be adjusted by the clinician. As mentioned above, the color of background component 314 and number component 312 of central section 310 may be based at least in part on the threshold comparisons described above for group section 328 where the comparisons in group section 328 may receive a different weighting than the other group sections 320.

With continued reference to FIG. 3, group section 330 displays a symbol 352 which includes both O$_2$ and CO$_2$ and identifies to the clinician that group section 330 is related to the gas exchange rates of O$_2$ and CO$_2$ by the patient. As an example, the color of a background 354 displayed by group section 330 may be based on a comparison of a ratio of the SpO$_2$ reading measured by the ventilator and the FiO$_2$ setting of the ventilator (SpO$_2$/FiO$_2$), the comparison of PaCO$_2$ input for arterial blood gas and etCO$_2$ (dead space) measurements, and/or the comparison of the ratio of etCO$_2$ and alveolar minute volume with pre-determined or adjustable thresholds. The thresholds may be adjusted by the clinician as necessary for a particular patient or patient condition. Examples of some thresholds for the SpO$_2$/FiO$_2$ ratio include an SpO$_2$/FiO$_2$ ratio greater than 400 which may indicate that the patient has a normal O$_2$ gas exchange and may be displayed by background 354 as the color green, an SpO$_2$/FiO$_2$ ratio from 300 to 400 which may indicate that the patient is experiencing a low O$_2$ gas exchange problem and may be displayed by background 354 as the color yellow, an SpO$_2$/FiO$_2$ ratio from 200 to 300 which may indicate that the patient is experiencing a moderate O$_2$ gas exchange problem and may be displayed by background 354 as the color orange, and an SpO$_2$/FiO$_2$ ratio less than 200 which may indicate that the patient is experiencing a severe O$_2$ gas exchange problem and may be displayed by background 354 as the color red.

One method for determining gas exchange function of the lung for CO$_2$ is to calculate the physiologic dead space. Physiologic dead space is the sum of alveolar dead space and anatomic dead space. An estimate of the anatomic dead space can be made using an assumption based on the patient's body weight, for example, 1 mL/lb. of body weight. A calculation of alveolar dead space can be made using the measurements of PaCO$_2$ and eTCO$_2$ using the following equation:

$$\frac{V_{alveolar\ dead\ space}}{V_t} = \frac{P_{aCO_2} - P_{end\ tidal\ CO_2}}{P_{aCO_2}} \quad (1)$$

The anatomic dead space added to the alveolar dead space yields the physiologic dead space. Examples of some thresholds that may be used for the ratio of physiologic dead space to tidal volume of the patient include from 0.2 to 0.35 which may indicate that the patient has normal CO$_2$ gas exchange and may be displayed by background 354 as the color green, from 0.35 to 0.55 which may indicate that the patient is experiencing a moderate CO$_2$ gas exchange problem and may be displayed by background 354 as the color yellow, and greater than 0.55 which may indicate that the patient is experiencing a severe CO$_2$ gas exchange problem and may be displayed by background 354 as the color red.

Another method of determining the patient's CO$_2$ gas exchange includes a comparison of thresholds for PaCO$_2$ and alveolar minute volume. Examples of some thresholds include, a PaCO$_2$ less than or equal to 45 mmHg, for a normal alveolar minute volume of 120 mL/min/Kg, assuming normal CO$_2$ production, the patient's CO2 gas exchange may be considered normal and may be displayed by background 354 as the color green, a PaCO$_2$ greater than 45 mmHg and less than 55 mmHg, with an alveolar minute volume greater than or equal to 120 mL/min/Kg and less than or equal to 140 mL/min/Kg may indicate that the patient is experiencing a moderate CO$_2$ gas exchange problem and may be displayed by background 354 as the color yellow, and a PaCO$_2$ greater than or equal to 55 mmHg with an alveolar minute volume greater than 120 mL/min/Kg may indicate a severe CO$_2$ gas exchange problem and may be displayed by background 354 as the color red.

The color of background 354 may also be based on the combination of the SpO$_2$/FiO$_2$ ratio, the PaCO$_2$ value, the etCO$_2$ value, and/or the alveolar minute volume where, for example, a patient experiencing a moderate O$_2$ gas exchange problem and a moderate CO$_2$ gas exchange problem may have background 354 displayed as the color red even though, when taken individually, background 354 would be displayed as the color yellow or orange. The number of thresholds and the threshold values for displaying different colors in background 354, and the colors to be displayed for each threshold may be adjusted by the clinician. As mentioned above, the color of background component 314 and number component 312 of central section 310 may be based at least in part on the threshold comparisons described above for group section 330 where the comparisons in group section 330 may receive a different weighting than the other group sections 320.

Any of the thresholds for changing the color of backgrounds 338, 342, 346, 350, and 354 and any of the colors for each threshold may be adjusted by the clinician to customize pictogram 300 for a particular patient or clinical setting.

Although the visual indicators for the backgrounds of group sections 320 are described above with respect to a color-coded status indicator, shape based status indicators or other similar status indicators are also contemplated. For example, the shape of each group section 320 may also or alternatively change based on the various thresholds described above to indicate a status of the group section 320 without departing from the scope of the present disclosure.

The clinician may also select or activate central section 300 or any of group sections 320, for example, by touching a particular group section 320 when UI 218 is displayed on a touch sensitive screen or by using an input device to select the particular group section 320. Activating a group section 320 may provide the clinician with additional patient status information relating to the particular group section 320 that is selected or activated including, for example, graphs, specific data and values, trending over time, etc. For example, as show in FIG. 4, if group section 346 is selected or activated by the clinician, an information window 356 may be displayed which provides a clinician with more detailed status information relating to the values of the parameters in group section 346, i.e., Vt and Pplat. Information window 356 may be an extension of pictogram 300 or may alternatively be displayed separately from pictogram 300. Activating central section 300 or any of group sections 320 may also provide additional patient status information relating to the patient's medical background, disease history, or other similar information that may be useful for the clinician to make an assessment of the patient's status.

Figure 4:
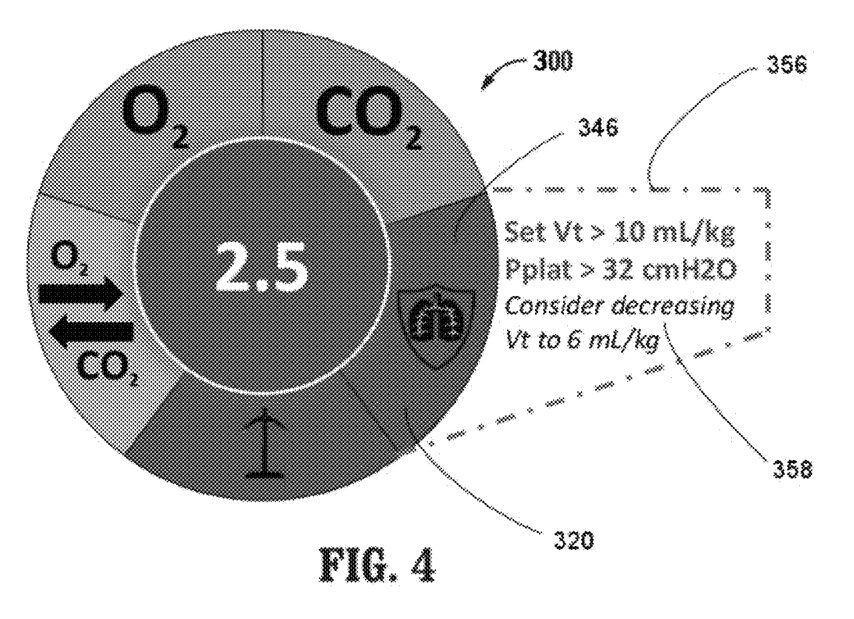
FIG. 4 illustrates the pictogram of FIG. 3 including a window for displaying additional information to a user.

Activating any one of group sections 320 may also provide the clinician with a potential course of action 358 to consider in response to changes in the particular group section 320 that is activated. Referring again to the example shown in FIG. 4, when group section 346 is activated by the clinician, a potential course of action 358 may be provided to the clinician in information window 356 along with the detailed status information. For example, the information window 356 may indicate to the clinician that a potential course of action 358 is to decrease set Vt to 6 ml/kg, as shown in FIG. 4. The potential course of action 358 presented to the clinician for consideration may be based on empirical evidence collected by the system 10 over the course of evaluating patients, clinical standards as promulgated by governmental agencies, medical associations, internally-generated protocols, published clinical studies, and from any other relevant medical source. The clinician may also be provided with a trend option that displays a trend of the selected group section 320 over time, e.g., a trend over time of color changes for the selected group section 320. The trend option may alternatively or additionally display a trend over time for the values of central section 310 and/or the pictogram 300 as a whole including each displayed group section 320 and central section 310.

Figure 5:
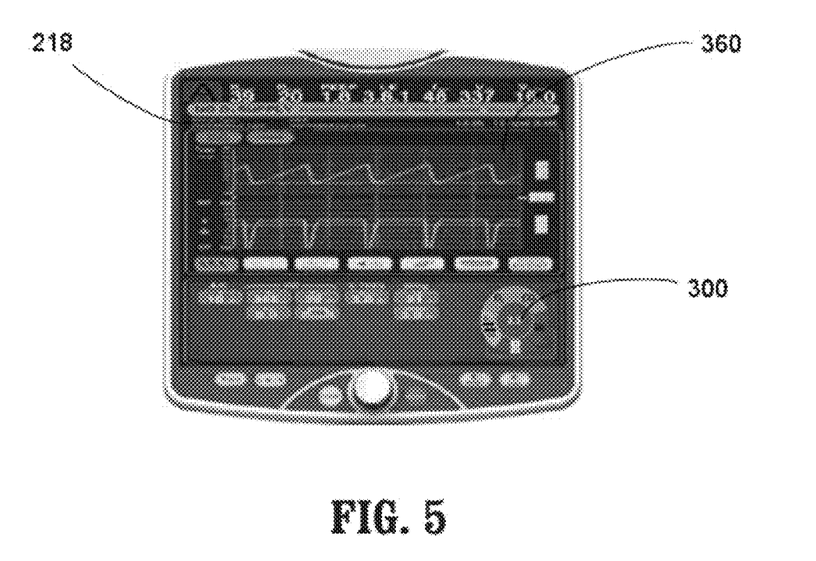
FIG. 5 illustrates a screen for providing additional information upon selection of a group section of the pictogram of FIG. 3.

In addition, when activating any of group sections 320, the clinician may be presented with the option to review a detailed information screen 360 in GUI 218 on any of the displays described above including graphs, data, trends over time, or other information relating to the parameters of the selected group section 320, as shown, for example, in FIG. 5. Detailed information screen 360 may provide the clinician with additional information relating to the parameters associated with a particular group section 320 of pictogram 300 and may also provide the clinician with information or additional parameters that while relevant may not be directly associated with the color-coding thresholds for the selected group section 320. In one embodiment, activating group sections 320 may include activating a hyperlink to detailed information screen 360 which may be stored on servers 140, 150, 160 and updated through wired or wireless connections as described above. The hyperlink may alternatively direct the clinician to the source of the parameter in the selected group section 320, for example, to display 128 of the pulse oximeter 126. Displaying detailed information screen 360 may replace the display of pictogram 300, or alternatively, pictogram 300 may be displayed in reduced size on a portion of detailed information screen 360 to continue providing the clinician with a concise assessment of the patient's overall status, as shown, for example, in FIG. 5.

With reference again to FIGS. 1 and 3, changes in the color-coding of pictogram 300 due to threshold changes in group sections 320 or central section 310 may trigger prompts or alerts to be transmitted from ventilator system 112 to servers 140, 150, 160, and/or any of remove devices 170, for example, to clinician devices, nursing stations, or a central alarm server, which may notify a clinician or other medical personnel of the change in the patient's status. For example, the clinician may be notified via a popup prompt on a remote device 170, e-mail, sms, a pager, or in a situation where the clinician cannot be reached electronically, a medical staff member may be sent to inform the clinician of the change in status.

While several embodiments of the disclosure have been shown in the drawings and described in detail hereinabove, it is not intended that the disclosure be limited thereto, as it is intended that the disclosure be as broad in scope as the art will allow. Therefore, the above description and appended drawings should not be construed as limiting, but merely as exemplifications of particular embodiments. Those skilled in the art will envision other modifications within the scope and spirit of the claims appended hereto.

What is claimed is:

1. A system for displaying a status of a patient on ventilation, comprising:
a ventilator system configured to provide mechanical ventilation to a patient; and
a display device operatively associated with the ventilator system and configured to display a user interface including a pictogram having patient status information related to the ventilator system, the pictogram including a central section configured to display patient status information relating to an overall status of the patient and at least one group section configured to display patient status information relating to a particular category of ventilatory status parameters.

2. The system according to claim 1, wherein the central section includes a numerical component and a background component, the numerical component configured to display a numerical value corresponding to the overall status of the patient and the background component configured to display a visual indicator corresponding to the numerical component.

3. The system according to claim 2, wherein the background component is configured to display a first visual indicator when the numerical value is greater than a first threshold and at least a second visual indicator when the numerical value is less than or equal to the first threshold.

4. The system according to claim 1, wherein the at least one group section includes a background configured to display a visual indicator corresponding to the patient status information relating to the particular category of ventilatory status parameters.

5. The system according to claim 4, wherein the background is configured to display a first visual indicator when at least one parameter of the patient status information relating to the particular category of ventilatory status parameters is greater than a second threshold and at least a second visual indicator when the at least one parameter of the patient status information of the particular category of ventilatory status parameters is less than or equal to the second threshold.

6. The system according to claim 1, wherein the patient status information displayed in the central section is generated based at least in part on the patient status information of the at least one group section.

7. The system according to claim 1, wherein the central section and/or at least one group section is configured for activation by a user to display additional patient status information relating to the overall patient status and the particular category of ventilatory status parameters.

8. The system according to claim 7, wherein the additional patient status information is selected from the group consisting of an overall patient status value, a ventilatory status parameter value corresponding to the particular category, a trend of the overall patient status value over time, a trend of the ventilatory status parameter value over time, a graph of the overall patient status value over time, a graph of the ventilatory status parameter value over time, a patient medical record, or a patient disease history.

9. The system according to claim 7, wherein the additional information includes a potential course of action for a user's consideration.

10. The system according to claim 1, wherein the at least one group section includes a symbol identifying the at least one group section as corresponding to the particular category of ventilatory status parameters.

11. The system according to claim 1, wherein the ventilatory system is configured to transmit an alert to a remote device when a value of the patient status information displayed by the central section or at least one parameter of the patient status information relating to the particular category of ventilatory status parameters displayed by the at least one group section changes relative to a threshold value.

12. A method of displaying a status of a patient on ventilation, comprising the steps of:
receiving ventilatory status parameters from at least one patient status monitoring device;
displaying a pictogram including a central section and at least one group section, the central section displaying an overall status of the patient based on the received ventilatory status parameters and the at least one group section displaying patient status information relating to a particular category of the received ventilatory status parameters;
changing a visual indicator of a background of the at least one group section in response to a change in at least one parameter of the particular category of the ventilatory status parameters relative to a first threshold; and
changing a visual indicator of a background component of the central section based on a change in a value of a numerical component of the central section relative to a second threshold, the value of the numerical component based at least in part on the at least one parameter of the particular category of the ventilatory status parameters.

13. The method according to claim 12, further including activating the central section and/or the at least one group section to display additional patient status information relating to the overall patient status and the particular category of the received ventilatory status parameters.

14. The method according to claim 13, wherein the additional patient status information includes a potential course of action for consideration by a user.

15. The method according to claim 13, wherein the additional patient status information includes at least one of an overall patient status value, a value of the at least one parameter of the particular category of the ventilatory status parameters, a trend of the overall patient status value over time, a trend of the value of the at least one parameter over time, a graph of the overall patient status value over time, a graph of the value of the at least one parameter over time, a patient medical record, or a patient disease history.

16. The method according to claim 12, wherein the at least one patient status monitoring device includes at least one of a ventilator, a pulse oximeter, a temperature sensor, or a capnograph.

17. The method according to claim 12, further including transmitting an alarm to a remote device when at least one of a color of the background of the at least one group section changes or a color of the background component of the central section changes.

18. A non-transitory computer-readable storage medium encoded with a program that, when executed by a processor, causes the processor to perform the steps of:
receiving ventilatory status parameters from at least one patient status monitoring device;
displaying a pictogram including a central section and at least one group section, the central section displaying an overall status of the patient based on the received ventilatory status parameters and the at least one group section displaying patient status information relating to a particular category of the received ventilatory status parameters;
changing a visual indicator of a background of the at least one group section in response to a change in at least one parameter of the particular category of the ventilatory status parameters relative to a first threshold; and
changing a visual indicator of a background component of the central section based on a change in a value of a numerical component of the central section relative to a second threshold, the value of the numerical component based at least in part on the at least one parameter of the particular category of the ventilatory status parameters.

19. The medium according to claim 18, further including activating the at least one group section to display additional patient status information relating to the particular category of the received ventilatory status parameters.

20. The medium according to claim 18, wherein the additional patient status information includes at least one of a value of the at least one parameter of the particular category of the ventilatory status parameters, a trend of the value over time, a graph of the value, a potential course of action for consideration by a user, a patient medical record, or a patient disease history.

* * * * *